United States Patent [19]
Gopalsami et al.

[11] Patent Number: 5,468,964
[45] Date of Patent: Nov. 21, 1995

[54] MILLIMETER WAVE SENSOR FOR MONITORING EFFLUENTS

[75] Inventors: Nachappa Gopalsami, Naperville; Sasan Bakhtiari, Bolingbrook; Apostolos C. Raptis; Stephen L. Dieckman, both of Downers Grove, all of Ill.

[73] Assignee: The University of Chicago, Chicago, Ill.

[21] Appl. No.: 262,998

[22] Filed: Jun. 20, 1994

[51] Int. Cl.$^6$ .................................................. G01N 22/00
[52] U.S. Cl. ........................................ 250/393; 250/336.1
[58] Field of Search ............................... 250/393, 336.1, 250/338.5

[56] References Cited

U.S. PATENT DOCUMENTS

4,287,418  9/1981  Orvin et al. ........................ 250/336.1

*Primary Examiner*—Carolyn E. Fields
*Attorney, Agent, or Firm*—Emrich & Dithmar

[57] ABSTRACT

A millimeter-wave sensor for detecting and measuring effluents from processing plants either remotely or on-site includes a high frequency signal source for transmitting frequency-modulated continuous waves in the millimeter or submillimeter range with a wide sweep capability and a computer-controlled detector for detecting a plurality of species of effluents on a real time basis. A high resolution spectrum of an effluent, or effluents, is generated by a deconvolution of the measured spectra resulting in a narrowing of the line widths by 2 or 3 orders of magnitude as compared with the pressure broadened spectra detected at atmospheric pressure for improved spectral specificity and measurement sensitivity. The sensor is particularly adapted for remote monitoring such as where access is limited or sensor cost restricts multiple sensors as well as for large area monitoring under nearly all weather conditions.

12 Claims, 7 Drawing Sheets

MILLIMETER WAVE SENSOR FOR MONITORING EFFLUENTS

FIELD OF THE INVENTION

This invention relates generally to the detection and measurement of effluents under atmospheric conditions and is particularly directed to a millimeter-wave sensor for monitoring airborne effluents within the atmosphere or at a process plant either remotely or locally.

BACKGROUND OF THE INVENTION

Detection of chemical and nuclear proliferation activities is a key issue in arms control treaty verification. There is a great need for remote sensing techniques that can determine airborne effluent signatures of a processing plant. Remote millimeter-wave spectroscopy offers great potential for this application because the millimeter-waves can penetrate through the atmosphere and can operate under all-weather conditions, including day or night times.

The Clean Air Act Amendments of 1990 dictate many new regulations, of which one that will have a significant impact on process industries is the requirement for continuous emissions monitoring devices. The availability of chemical sensors for stack gas or effluent monitoring is very limited. Most are species-specific and point-type sensors. In addition to in-stack monitoring, there is a need for standoff, wide-area monitoring of chemicals that are released from stacks and vents of process and waste treatment plants. Such a sensor will not only provide a demonstration of environmental compliance, but also will serve as an indicator of impending runaway reactions and of inefficient process conditions.

Fourier-transform infrared (FTIR) techniques are currently being explored for stack-gas monitoring. Laboratory FTIR instruments are being modified for field applications. Compared to infrared techniques that mainly show vibrational bands of molecular functional groups, the millimeter-wave spectra are generally unique to a molecule and often simpler to interpret because there are no complications with respect to vibrational or electronic transitions. There are no moving parts as in FTIR, so the millimeter-wave sensor is less affected by floor vibrations and maintenance is easier. Millimeter-wave techniques can be used in smoky and dusty environments. Millimeter-waves can transit thick dielectric walls and particulate laden gases. Optical techniques require transparent windows which must be cleaned or purged periodically. Also, millimeter radiation is less affected by dust and cloud conditions, and can provide longer detection ranges. There are three broad atmospheric windows in the millimeter range, centered around 94, 140 and 270 GHz, which can be used for remote measurements without much atmospheric attenuation and interference.

Millimeter-wave spectroscopy is an established technique for determining the structure and dynamics of molecules in the gas or vapor phase. Polar molecules selectively absorb electromagnetic radiation of specific wavelengths in the millimeter and submillimeter-regions in accordance with their rotational energy transitions. Of all known analytical techniques, the millimeter-wave technique offers the highest possible spectral resolution if the analyte can be sampled and fed into a gas cell under low pressure. For example, typical line widths (half width at half maximum) of rotational lines are 4 kHz at one millitorr, and in a band width of 1 GHz, 250,000 resolution lines are available.

Millimeter-wave radiometers have been used by researchers for radioastronomical detection of molecules in interstellar clouds and for atmospheric sounding of temperature and density profiles using oxygen and water vapor molecules. See M. A. Janssen (Ed.), "Atmospheric Remote Sensing by Microwave Radiometry," John Wiley, New York (1993). Also a ground-based millimeter-wave sensor based on multispectral radiometry has been successfully employed to measure spectroscopic trace constituents such as HCN, ClO, and $HO_2$. See A. Parrish et al., "A Ground Based Technique for Millimeter-wave Spectroscopic Observations of Stratospheric Trace Constituents," Radio Science, Vol. 23, pp. 106–118 (1984). Concentrations of gases lower than parts per billion have been measured using this technique. Recently, millimeter-wave multispectral radiometers have been used in the NASA's upper atmospheric research satellite (UARS) and have provided the first global-scale map of chlorine monoxide in the lower stratosphere.

Under low pressures, the technique offers very high spectral specificity. But remote monitoring of chemicals in the air requires measurements to be made at ambient pressure (1 atm). The effect of increased pressure on the rotational line is twofold: one, it reduces the detection peak and two, it broadens the spectral line. As a result, the detection sensitivity and chemical selectivity suffer at high pressures. But these problems can be mitigated by using high frequency millimeter-waves with wide bandwidth. The detection sensitivity increases in general with the square of the frequency and the number of resolution lines (chemical selectivity) increases with wide bandwidths that are practical with high frequency millimeter-waves.

Significant advances have been made in microwave/millimeter-wave systems with applications to defense/space technology, meteorology, and remote sensing of the Earth. Combining the latest developments in high frequency sources in the millimeter and submillimeter-wave range, wide-sweep capability of the sources, and sensitive solid-state millimeter/submillimeter-wave detectors, this invention presents new millimeter/submillimeter-wave sensor approaches that can be successfully applied to remote or inplant spectroscopy at ambient pressures. Both active systems based on swept-frequency radar technique and passive systems based on multispectral radiometer techniques are presented.

OBJECTS AND SUMMARY OF THE INVENTION

Accordingly, it is an object of the present invention to provide an improved millimeter-wave sensor for detecting and measuring either remotely or locally a plurality of species of airborne effluents on a real time basis.

Another object of the present invention is to provide apparatus for continuously monitoring, under virtually any weather conditions, stack gas emissions using millimeter-waves which offers high degrees of detection sensitivity and component specificity.

Yet another object of the present invention is to provide improved spectral specificity and measurement sensitivity in monitoring and measuring airborne effluents by signal processing of measured spectra.

A further object of the present invention is to provide an arrangement for monitoring and measuring airborne effluents in the atmosphere or at a process plant at atmospheric pressure for mitigating pressure broadening of the spectral lines and the reduced sensitivity and specificity associated therewith.

These and other objects of the present invention are achieved by a method for determining the concentration of a chemical species in a gas plume, the method comprising the steps of: determining a low pressure spectra of the chemical species; determining a pressure broadened spectra of the chemical species as measured at atmospheric pressure; dividing a Fourier transform of the pressure broadened spectra by a Fourier transform of the low pressure spectra to provide a filter function for the chemical species; measuring a pressure broadened composite spectra of a gas plume of unknown composition; multiplying the Fourier transform of the composite spectra by an inverse of the filter function to provide a product function; and determining the inverse Fourier transform of the product function to provide the concentration of the chemical species in the gas plume.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF PREFERRED EMBODIMENT

Figure 1:
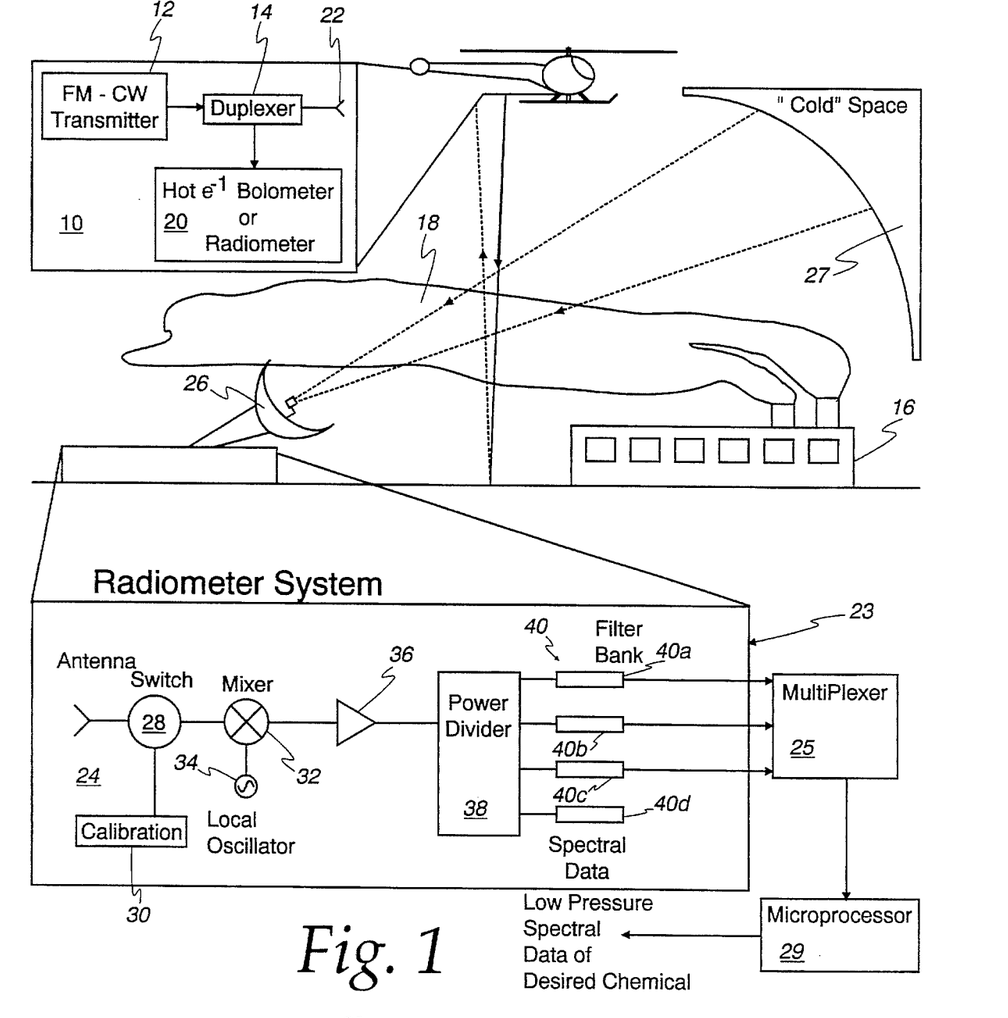
FIG. 1 is a simplified schematic diagram of an active and a passive millimeter-wave standoff sensor in accordance with the principles of the present invention.

FIG. 1 is a simplified schematic illustration of standoff monitoring sensors based on both active and passive spectroscopy in accordance with the present invention. In the active mode, a millimeter-wave source/receiver 10 transmits frequency-modulated continuous waves toward a plume 18 containing the chemicals to be detected. Plume 18 is emitted by a plant or factory 16. Millimeter-wave source/receiver 10 includes an FM-CW transmitter 12, a duplexer 14, and an antenna 22. The signal reflected or backscattered from the ground is received by a hot electron bolometer or a wideband radiometer 20 within the millimeter-wave source/receiver 10. Since the radiometer 20 is very sensitive with a noise equivalent power of less than $10^{-15}$ W, the radar-radiometer combination provides excellent sensitivity for detecting weak radar return signals which transit plume 18 twice.

The hot electron bolometer 20 is a solid state device typically comprised of indium antimonide which is heated when millimeter-wave power is received. The electrical conductivity of bolometer 20 changes with its temperature which provides a measure of the intensity of the received millimeter-wave power. Bolometer 20 is typically cooled with liquid helium to provide a very sensitive detector over a wide bandwidth typically on the order of 200–300 GHz. Where a radiometer is employed in the millimeter-wave source/receiver 10, the radiometer downconverts the high frequency (HF) to an intermediate frequency (IF) and does not typically require cooling. A radiometer is characterized by less noise than a bolometer, although it does not operate at the large bandwidths of a bolometer.

A passive millimeter-wave spectroscopy system 23 uses a multispectral radiometer 24 for measuring the emission temperature of plume 18 with respect to frequency. Because radiometer 24 receives, in addition to the molecular emissions, the thermal (blackbody) radiation from the background scene in the antenna footprint, the effect of background plays an important role. In general, better contrast is obtained if the plume 18 is viewed against a cold sky 27 or if the emissivity of the background scene is much less than one. Because the emissivity of ground materials at millimeter-wavelengths is generally less than one, the passive system can also be deployed in a flyby mode. Computer simulation of expected emission temperatures for typical plume gases has been made with realistic assumptions on the background.

Coupled to the multispectral radiometer 24 is an antenna 26 for receiving emissions from plume 18. Antenna 26 as well as a calibration unit 30 are coupled to a switch 28. The calibration unit 30 allows for periodic calibration of the radiometer system 24. The received millimeter-wave signal is provided to a mixer 32 where it is combined with the output of a local oscillator 34 to provide an intermediate frequency (IF) signal which is provided via an amplifier 36 to a power divider 38. In the disclosed embodiment used for proof of principle test, the local oscillator was at 85.3 GHz and the received signal was in the frequency range of 77.3–83.3 and 87.3–93.3 GHz, with a bandwidth on the order of 6 GHz. The IF signal was in the range of 2–8 GHz and was fed by the power divider 38 to a filter bank 40 comprised of spectral filters 40a, 40b, 40c and 40d. The 6 GHz bandwidth of the IF signal is thus divided into on the order of 500 MHz sub-band increments for measuring the power within the several sub-bands. The proof of principle of using the radiometer in the passive mode as well as a receiver in the active mode was successfully tested in the laboratory.

Figure 2:
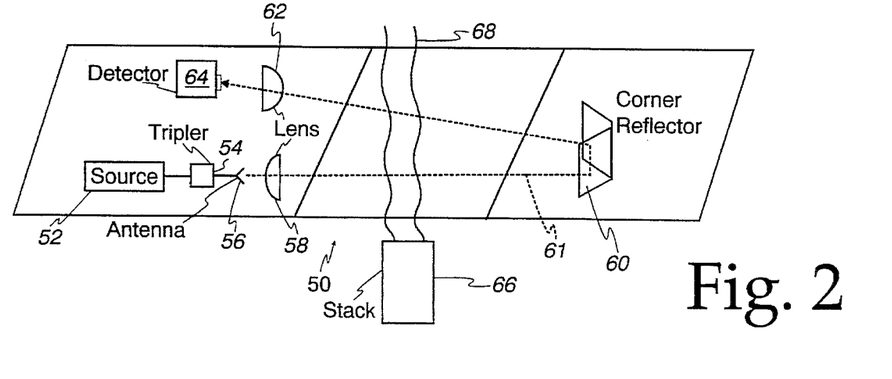
FIG. 2 is a simplified schematic diagram illustrating an active millimeter-wave stack gas sensor in accordance with one embodiment of the present invention.
Figure 3:
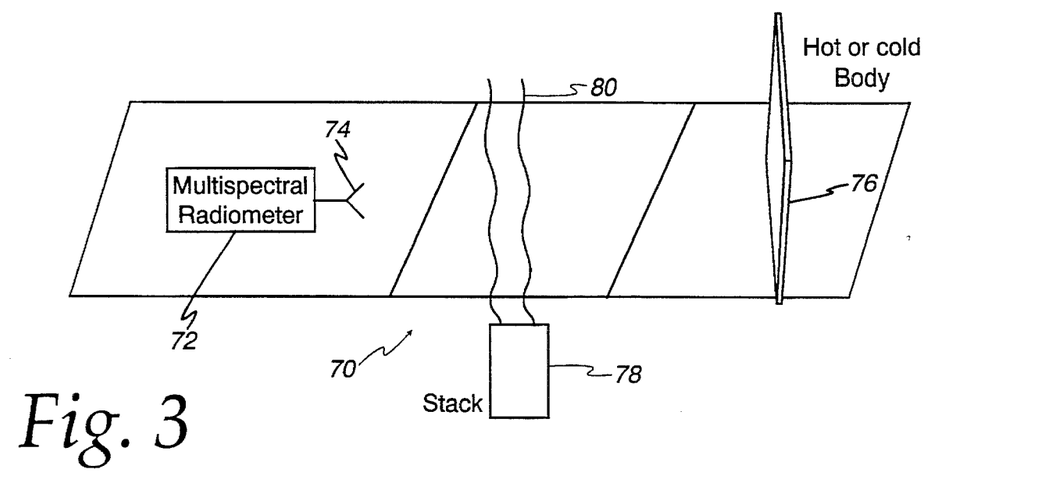
FIG. 3 is a simplified schematic illustration of a passive millimeter-wave stack gas sensor in accordance with another embodiment of the present invention.

FIGS. 2 and 3 are simplified schematic diagrams of in-place monitoring sensors based on active and passive sensors, respectively. An active sensor 50 shown in FIG. 2 uses a retroreflector 60 mounted on the far side of the plume 68. A swept-frequency signal is transmitted through the plume 68 of interest and received back using a corner retroreflector 60. In the case of a passive sensor 70 as shown in FIG. 3, a multispectral radiometer 72 receives the molecular emission of plume 80 emitted from stack 78 against a hot or cold blackbody 76.

Coupled to the radiometer system 24 is the combination of a multiplexer 25 and a microprocessor 29. A similar combination of a multiplexer and microprocessor is also coupled to the radiometer 20 of the millimeter-wave source/receiver 10 or a microprocessor alone if a hot electron bolometer is used, but has been omitted from the figure for simplicity. Multiplexer 25 is coupled to the spectral filters 40a–40d for providing each sub-band signal to microprocessor 29. Microprocessor 29 processes the output spectral signals in accordance with the present invention, including deconvoluting the measured spectra as described in detail below, to provide low pressure spectral data of the chemical species in gas plume 18.

Figure 4:
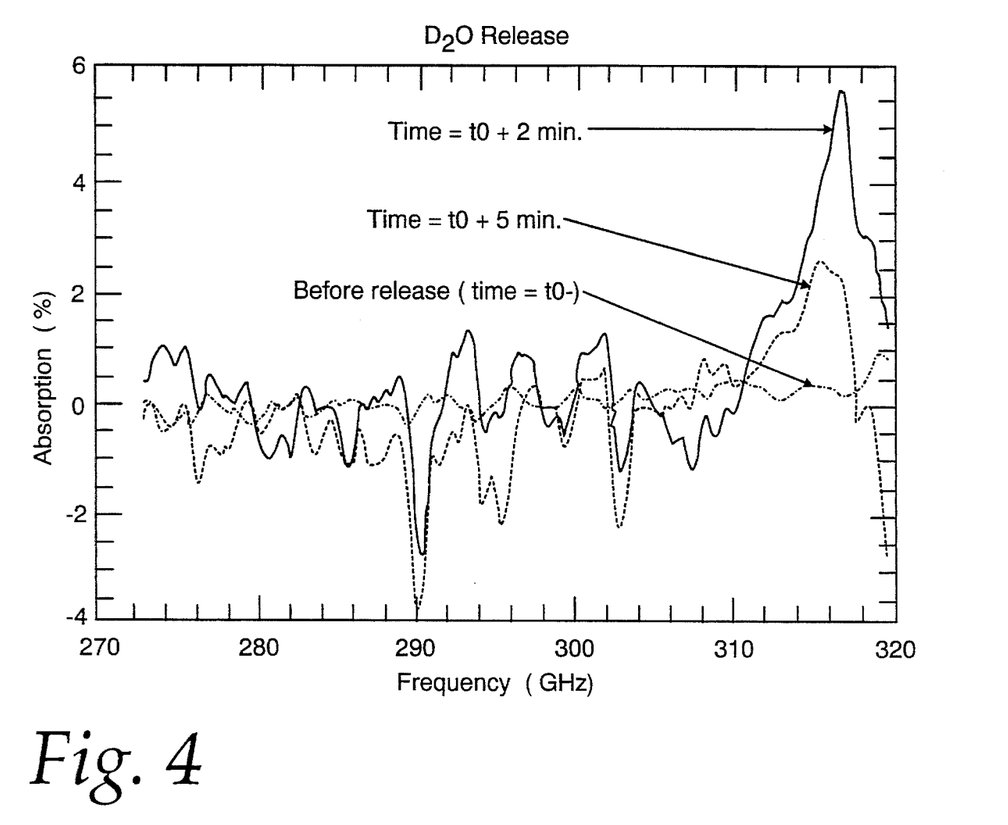
FIG. 4 is a graphic representation of the measurement of $D_2O$ release when heated in a beaker with a decreasing release rate with time as measured by the millimeter-wave sensor of the present invention.
Figure 5:
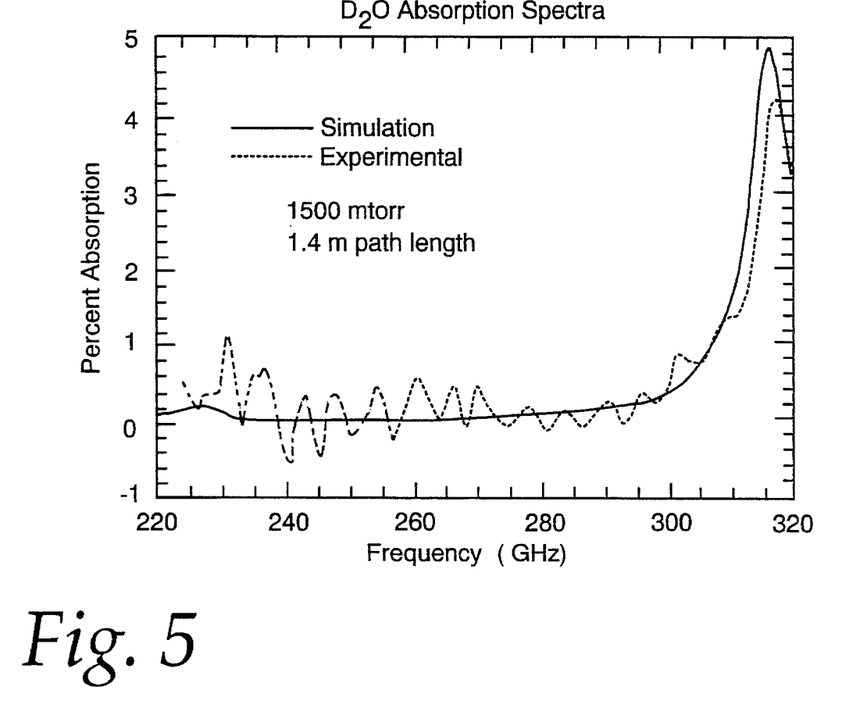
FIG. 5 is a graphic comparison of a simulated and measured $D_2O$ absorption spectra as measured in a gas cell by the millimeter-wave sensor of the present invention.

The proof of principle of the active sensor 50 in FIG. 2 was tested in the laboratory. The source 52 was a millimeter-wave sweeper in the 75–110 GHz range, the output of which is passed through a frequency tripler 54 generating frequencies in the range of 225–330 GHz. The millimeter-wave beam 61 was then transmitted through a plume 68 such as emitted by a stack 66. A corner reflector 60 on the far side of the plume 68 returns the radiation back to a hot-electron-bolometer receiver/detector 64. Lenses 58 and 62 were used to respectively collimate and focus the millimeter-wave beam 61. The plume 68 was created by heating $D_2O$ in a beaker (not shown) and releasing the $D_2O$ vapor in the path of the millimeter-wave beam 61. FIG. 4 illustrates the measurement results as the $D_2O$ release rate decreases with time. For comparison, a graphic comparison of a simulated $D_2O$ absorption spectra and the measured $D_2O$ absorption spectra in a gas cell is shown in FIG. 5. An estimate of release concentrations based on FIG. 5 is from 2 to 8 parts per thousand over a pathlength of 0.5 meters.

Figure 7:
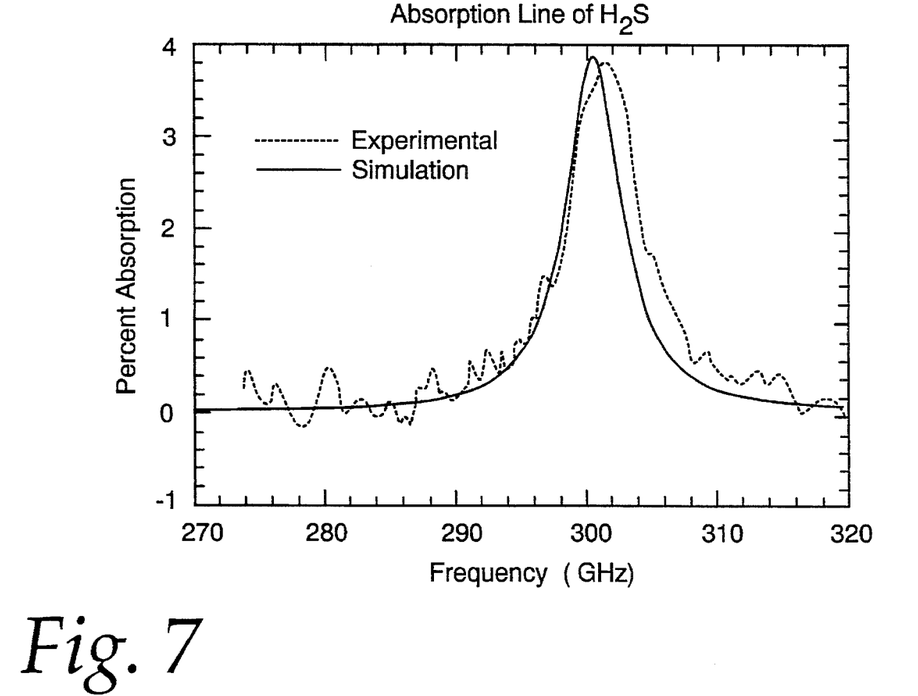
FIG. 7 is a graphic comparison of a simulated and measured absorption line of $H_2S$ as measured by the millimeter-wave sensor of the present invention.
Figure 8:
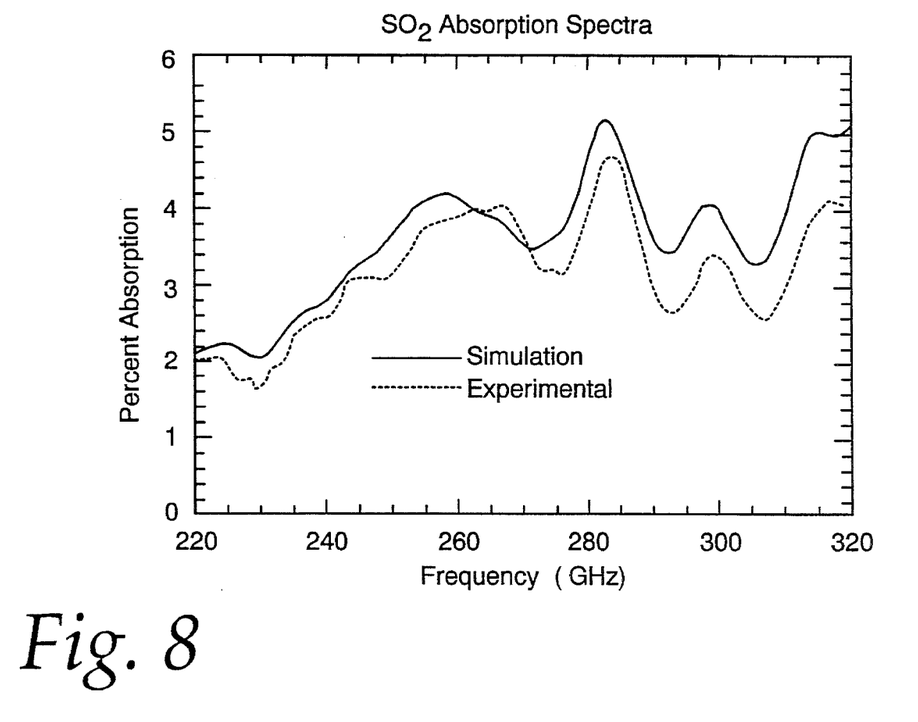
FIG. 8 is a graphic comparison of a simulated and measured absorption spectra of $SO_2$ as measured by the millimeter-wave sensor of the present invention.

Millimeter-wave sensitivities of several organic and inorganic chemicals have been tested in the laboratory within the 220–320 GHz frequency range. For analysis purposes, the molecules may be classified into two groups, those that have spectral lines far apart in the frequency space and consequently resolvable even under pressure broadening and those that have dense lines and are not individually resolvable. Simple molecules like HCN and $H_2S$ belong to the first group, while complex and heavy molecules like $SO_2$ and ethanol belong to the second group. The simulated and measured absorption strengths of HCN and $H_2S$ are given in FIGS. 6 and 7, respectively. The experimental measurements were made using a millimeter-wave detector in accordance with the present invention in a 1.45-meter long gas cell with a partial pressure of 1.5 torr of the chemical mixed with 758.5 torr of nitrogen, i.e., an equivalent of 0.833 ppm of the chemical over a km path length in the atmosphere. Using low pressure data from a Jet Propulsion Laboratory database, the simulation was performed by applying a Lorentzian line shape function for each line and then summing the spectral values at each frequency. Figure 8 graphically illustrates the simulated and measured spectral characteristics of $SO_2$. The spectral lines of $SO_2$ are dense and overlap under pressure broadening. Interestingly, the dense lines of the molecules aggregate themselves into characteristic band heads under pressure broadening. This is a very useful result because it shows that the millimeter-wave sensor of the present invention can be used for both light and complex molecules.

The detection sensitivity varies with the type of molecule and the transition frequency. In general, molecules like HCN having light weight and high dipole moment provide a high sensitivity of detection with individually resolvable spectral lines. More complex and heavier molecules have generally dense lines in the millimeter region and under pressure broadening are likely to aggregate into some characteristic band structures, as for example with $SO_2$ as shown in FIG. 8.

Figure 6:
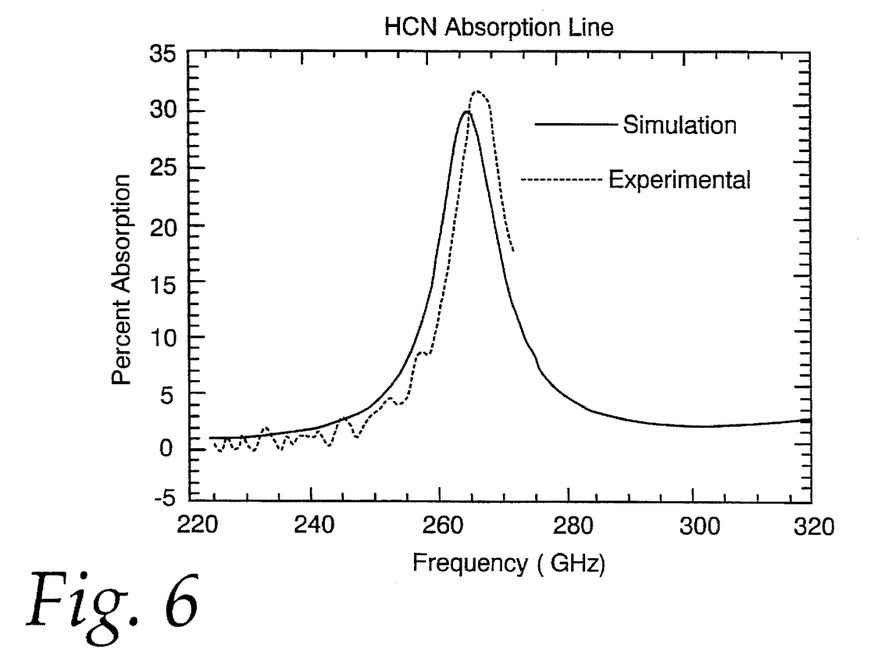
FIG. 6 is a graphic comparison of a simulated and measured HCN absorption line as measured by the millimeter-wave sensor of the present invention.
Figure 9:
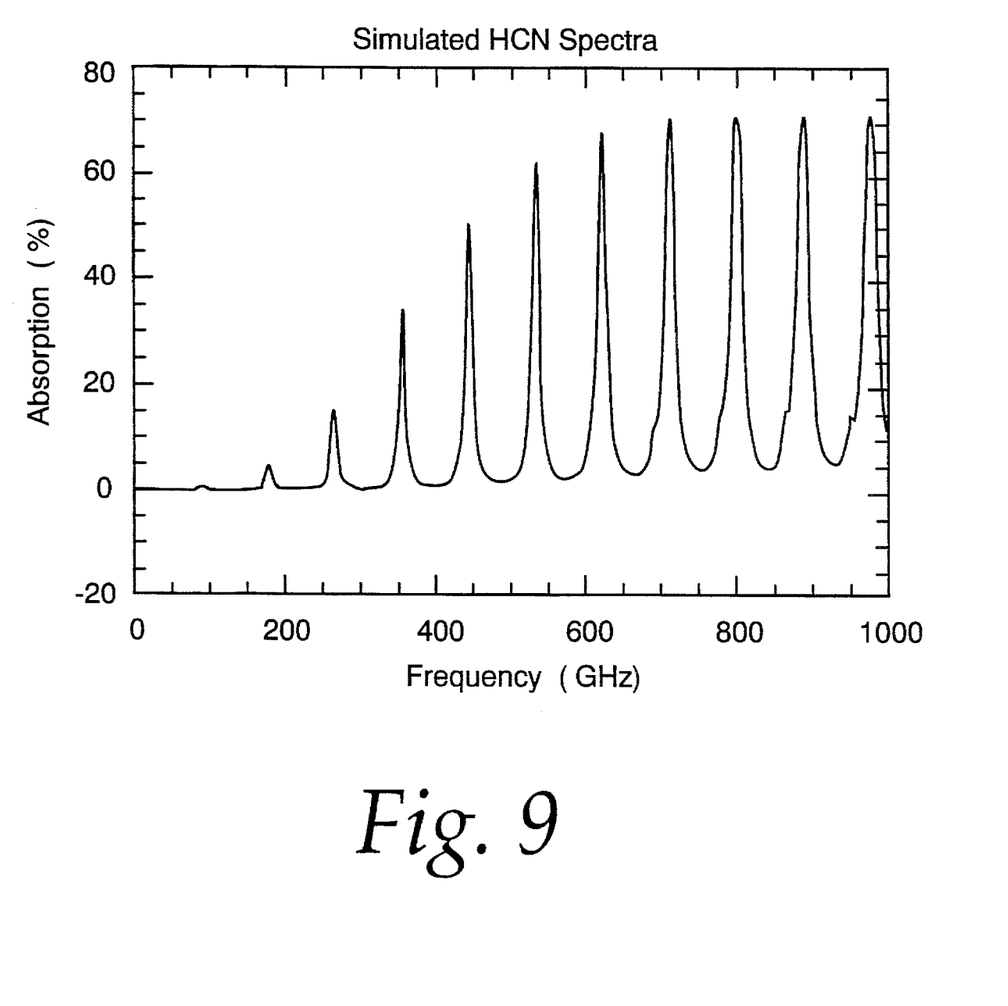
FIG. 9 is a graphic representation of a simulated HCN spectra at 30 to 1000 GHz.

From the measured absorption line of HCN in FIG. 6, the absorption coefficient is 0.188 $m^{-1}$ for 1 torr of partial pressure. If the measurement system can detect 0.1 percent change in absorption, the detection sensitivity of HCN is calculated to be 7 ppm over a meter pathlength. The sensitivity of detection increases with frequency and pathlength, see for instance FIG. 9, which is a theoretically simulated plot of spectral lines of 1 torr of HCN in the 30–1000 GHz range for 1 meter pathlength.

The selectivity of the technique for detection of individual molecules is important because a sensor must detect and quantify chemicals in a mixture. Multivariate regression analysis is a useful technique for analysis of chemical mixtures if the number and type of chemicals in the mixture are known a priori. For example, a partial least squares algorithm has yielded accurate results in the quantification of individual chemicals in a simulation study conducted on a composite spectra of 11 chemicals.

Figure 10A:
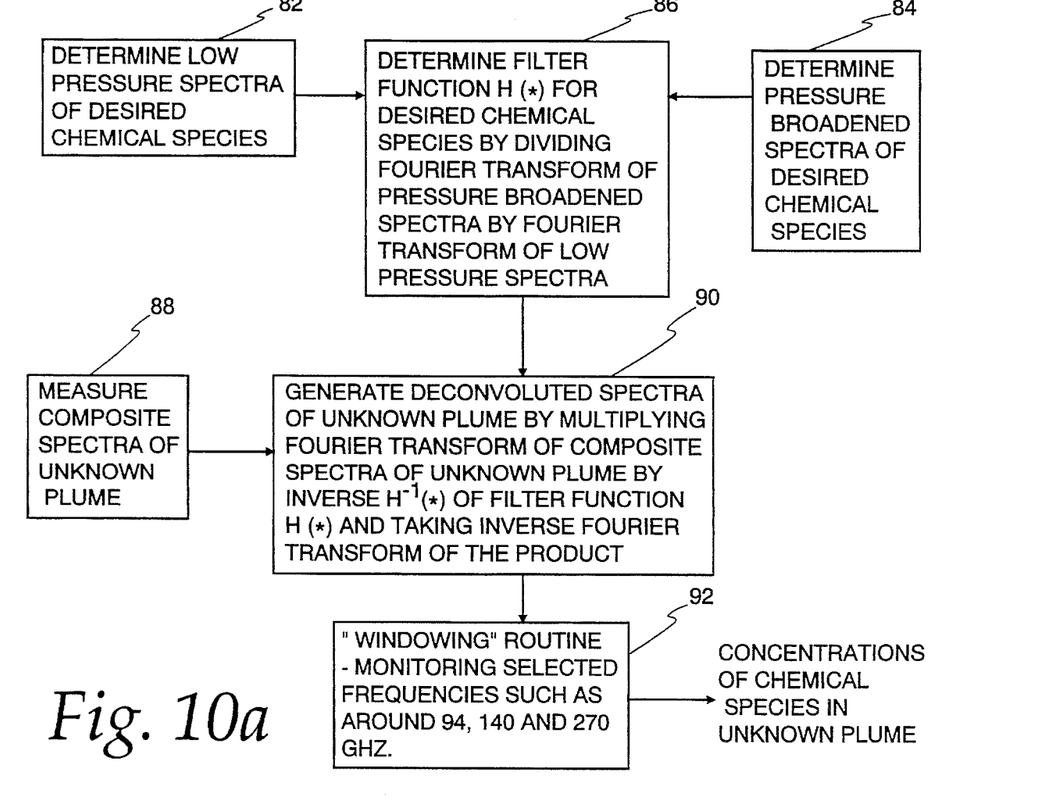
FIG. 10a is a flow chart illustrating the steps in carrying out the method for monitoring effluents using a millimeter-wave sensor in accordance with the present invention.

More important for arms control applications is the capability to detect the presence of certain target chemicals in an unknown plume. The present invention employs a novel signal processing algorithm based on deconvolution to detect certain target chemicals in an unknown plume. FIG. 10a gives the deconvolution procedure, wherein the relationship between the low pressure and pressure-broadened spectra are first obtained in the form of a filter function H(·). The pressure-broadened spectra of a chemical may be viewed as the filtered response of its low-pressure spectra. See FIG. 10b. Depending on their line locations and line widths, the filter characteristics will be different for different chemicals. An inverse filtering or deconvolution is performed on the unknown composite spectra to determine the corresponding low-pressure spectra of the desired chemical. Because the deconvolved spectra have narrow line widths by two or three orders of magnitude compared to the pressure-broadened spectra, the spectral specificity is dramatically improved by this process. Furthermore, because the integrated intensity is the same for the low pressure and pressure broadened lines, the sensitivity of detection can also be improved by using the deconvolution procedure of the present invention.

Referring to FIG. 10a, there is shown a simplified flow chart illustrating the steps carried out by the microprocessor shown in FIG. 1 in the processing of the received spectral signal in accordance with the present invention. At step 82, the low pressure spectra of a desired chemical species 82 (one or more) is determined and is provided to the microprocessor such as by reading from a memory or entry by a system user. At step 84, the pressure-broadened spectra of a desired chemical species (one or more) are determined and also provided to the microprocessor. The operating program stored in the microprocessor then, at step 86, determines a filter function H(·) for the desired chemical species by dividing the Fourier transform of the pressure broadened spectra by that of the low pressure spectra. The filter function H(·) is a Fourier domain function. At step 88, the composite spectra of an unknown plume is measured and is used to generate a deconvoluted spectra of the unknown plume at step 90 by multiplying the Fourier transform of the measured composite spectra by an inverse filter function $H^{-1}(\cdot)$ of the filter function H(·) and by taking the inverse Fourier transform of the product. Next, at step 92 a "windowing" routine is executed where only selected frequencies, or frequency bands, are monitored in determining the composition of the gas plume. The concentration of any of the chemical species within the unknown plume can then be determined.

Figure 10B:
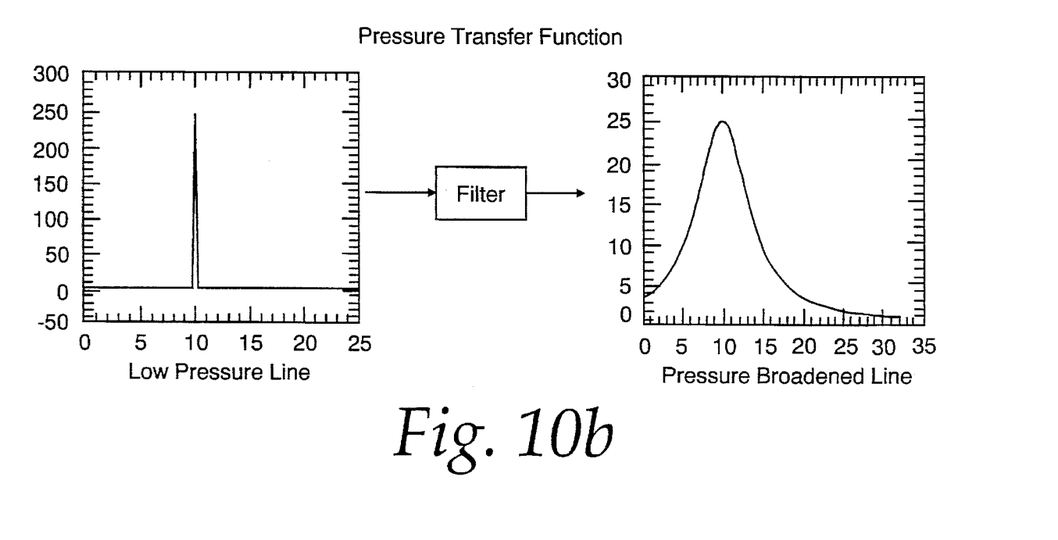
FIG. 10b is a simplified schematic and graphic illustration of the effect of a pressure transfer function on the measured spectra of a chemical species in accordance with one aspect of the present invention.

The pressure transfer function is defined in terms of various parameters and is given by the following expression:

$$\alpha(v) = \frac{(\alpha_{low} \Delta v_{low}) \Delta v_{high}}{(v - v_o)^2 + (\Delta v_{high})^2}$$

where $v$=frequency $v_o$=transition (or center) frequency $\alpha_{low}$=peak height of low pressure line $\Delta v_{low}$=line width at low pressure $\Delta v_{high}$=line width at high pressure. The transfer, or filter, function H(·) may be expressed in terms of the aforementioned pressure transfer function and allows for calculation of the pressure broadened line from a low pressure line as shown in simplified schematic form in FIG. 10b. The inverse $H^{-1}(\cdot)$ of the filter function H(·) allows for the reverse process and a narrowing of the pressure broadened line in the form of a low-pressure line for improved spectral resolution and plume component specificity.

Figure 11:
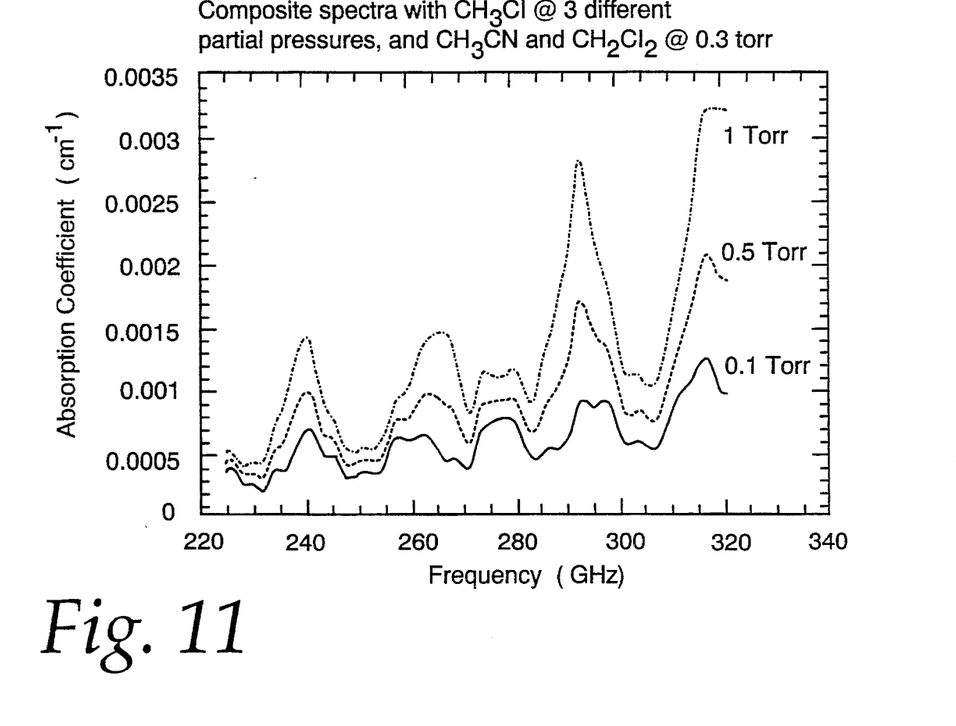
FIG. 11 is a graphic illustration of the composite spectra of three chemicals, $CH_3Cl$, $CH_3CN$, and $CH_2Cl_2$, wherein three different mixture data were generated by adding the individually measured data in appropriate proportions.
Figure 12:
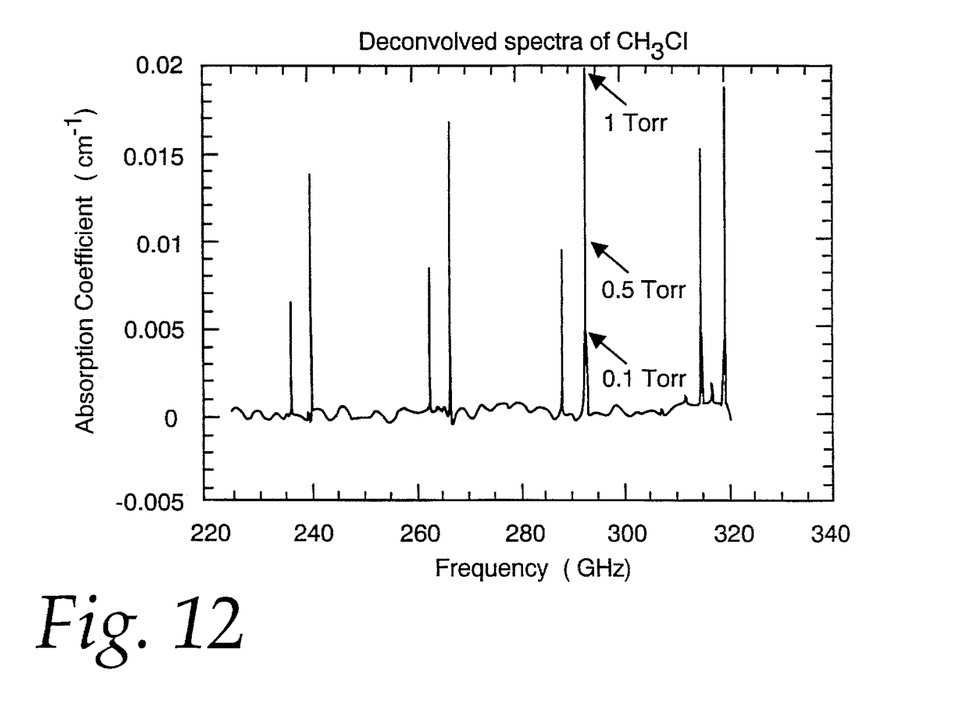
FIG. 12 is a graphic illustration of the deconvolved spectra of $CH_3Cl$ generated in accordance with the present invention.

The deconvolution method of the present invention was tested with measurement data. FIG. 11 shows composite spectra of three chemicals, $CH_3Cl$, $CH_3CN$, and $CH_2Cl_2$, wherein three different mixture data were created by adding the individually measured data in appropriate proportions. By applying deconvolution procedure on the mixture data, the chemical $CH_3Cl$, for example, was resolved as shown in FIG. 12. The line locations are exactly as they were in the low-pressure measurement data. More importantly, the spectra of the other two chemicals $CH_3CN$ and $CH_2CE_2$ are suppressed in the final results. The inventive signal processing technique thus results in accurate and highly resolved spectral lines.

There has thus been shown a millimeter-wave sensor and a method for monitoring airborne effluents such as from a process plant which allows for detection and measurement of effluents under atmospheric conditions performed either remotely or in-plant on a real time basis. The inventive millimeter-wave sensor arrangement includes a high frequency signal source for transmitting frequency-modulated continuous waves in the millimeter or sub-millimeter range with a wide sweep frequency capability and a detector with associated software to detect a plurality of species of effluents. The microprocessor controlled system employs a novel signal processing technique based on deconvolution to determine the high resolution spectra of an effluent, or effluents. The deconvolved spectra for an effluent has very narrow line widths by two or three orders of magnitude compared to pressure broadened spectra detected at atmospheric pressure to provide substantially improved spectral specificity and measurement sensitivity.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. A method for determining the concentration of a chemical species in a gas plume, said method comprising the steps of:

determining a low pressure spectra of the chemical species;

determining a pressure broadened spectra of said chemical species as measured at atmospheric pressure;

dividing a Fourier transform of said pressure broadened spectra by a Fourier transform of said low pressure spectra to provide a filter function for said chemical species;

measuring a pressure broadened composite spectra of a gas plume of unknown composition;

multiplying the Fourier transform of said composite spectra by an inverse of said filter function to provide a product function; and determining the inverse Fourier transform of the product function to provide the concentration of said chemical species in the gas plume.

2. The method of claim 1 wherein the step of measuring the composite spectra includes directing millimeter or submillimeter-waves through the gas plume.

3. The method of claim 2 further comprising the step of reflecting said millimeter or submillimeter-waves back through the gas plume.

4. The method of claim 2 wherein the step of measuring the composite spectra further includes directing a frequency-modulated continuous wave through the gas plume.

5. The method of claim 4 wherein the step of measuring the composite spectra further includes sweeping said frequency-modulated continuous wave over a frequency range of approximately 220–320 GHz.

6. The method of claim 1 further comprising the step of measuring the composite spectra of the gas plume over a plurality of discrete frequency ranges.

7. The method of claim 6 wherein said plurality of frequency ranges are centered at approximately 94, 140 and 270 GHz.

8. Apparatus for determining the composition of a gas plume at atmospheric pressure comprising:

a transmitter for directing a frequency-modulated, millimeter or sub-millimeter, continuous wave through the gas plume;

a receiver for receiving said continuous wave following its transit through the gas plume; and signal processing means coupled to said receiver for converting a pressure broadened spectra of the gas plume measured at atmospheric pressure to a low pressure spectra and comparing the low pressure spectra of the gas plume with a second low pressure spectra including selected components in determining the composition of the gas plume.

9. The apparatus of claim 8 further comprising a reflector for directing said continuous wave back through the gas plume to said receiver.

10. The apparatus of claim 9 wherein said reflector is a corner reflector.

11. The apparatus of claim 8 further comprising a first lens for collimating in said continuous wave prior to passage through the gas plume.

12. The apparatus of claim 11 further comprising a second lens for focusing said continuous wave on said receiver after transitting the gas plume.

\* \* \* \* \*